US010918555B2

(12) United States Patent
Konishi et al.

(10) Patent No.: US 10,918,555 B2
(45) Date of Patent: Feb. 16, 2021

(54) HEALTH PROMOTING APPARATUS

(71) Applicant: Sominoya, inc., Tokyo (JP)

(72) Inventors: Aoi Konishi, Tokyo (JP); Masahiro Akishita, Tokyo (JP); Yasuhiro Sawada, Tokorozawa (JP); Youngjae Ryu, Tokyo (JP); Takahiro Maekawa, Tokorozawa (JP); Shuhei Murase, Tokyo (JP); Takenobu Inoue, Tokorozawa (JP); Atsushi Takashima, Tokorozawa (JP); Jun Suzurikawa, Tokorozawa (JP)

(73) Assignee: Sominoya, inc., Tokyo (JP)

( * ) Notice: Subject to any disclaimer, the term of this patent is extended or adjusted under 35 U.S.C. 154(b) by 0 days.

(21) Appl. No.: 16/616,935

(22) PCT Filed: May 23, 2018

(86) PCT No.: PCT/JP2018/019809
§ 371 (c)(1),
(2) Date: Nov. 25, 2019

(87) PCT Pub. No.: WO2018/216723
PCT Pub. Date: Nov. 29, 2018

(65) Prior Publication Data
US 2020/0253806 A1    Aug. 13, 2020

(30) Foreign Application Priority Data
May 26, 2017    (JP) ................. 2017-104095

(51) Int. Cl.
A61H 1/00    (2006.01)
A61H 23/00   (2006.01)
A61M 21/02   (2006.01)

(52) U.S. Cl.
CPC .......... A61H 1/005 (2013.01); A61H 23/006 (2013.01); A61M 21/02 (2013.01);
(Continued)

(58) Field of Classification Search
CPC ............ A61H 1/005; A61H 2201/0149; A61H 2203/0456; A61H 2205/02; A61M 21/02
See application file for complete search history.

(56) References Cited

U.S. PATENT DOCUMENTS 6,155,976 A    12/2000    Sackner et al.

FOREIGN PATENT DOCUMENTS

CN    101132754 A    2/2008
EP    2052708 A1    4/2009
(Continued)

OTHER PUBLICATIONS

International Preliminary Report on Patentability and Written Opinion issued in PCT/JP2018/019809; dated Nov. 26, 2019.
(Continued)

Primary Examiner — Christine H Matthews
(74) Attorney, Agent, or Firm — Studebaker & Brackett PC

(57) ABSTRACT

A health promoting apparatus to benefit health of a user based on medical factors underlying moderate exercise, comprises: an oscillation generator configured to oscillate a head of the user in a vertical direction or an anteroposterior direction; and an oscillation controller connected to the oscillation generator, and configured to control the oscillation generated by the oscillation generator. The oscillation controller is configured to control the oscillation generator to apply a shear stress to cells in a brain of the user by moving interstitial fluid in the brain, in order to promote the health of the user.

3 Claims, 20 Drawing Sheets

(52) U.S. Cl.
CPC ............. *A61H 2201/0149* (2013.01); *A61H 2201/123* (2013.01); *A61H 2201/1215* (2013.01); *A61H 2201/1418* (2013.01); *A61H 2201/1607* (2013.01); *A61H 2201/1626* (2013.01); *A61H 2203/0406* (2013.01); *A61H 2203/0431* (2013.01); *A61H 2203/0456* (2013.01); *A61H 2205/02* (2013.01)

(56) References Cited

FOREIGN PATENT DOCUMENTS

| EP | 2986265 A1 | 2/2016 |
|---|---|---|
| JP | 2006-136515 A | 6/2006 |
| JP | 2008-079834 A | 4/2008 |
| JP | 2008-289756 A | 12/2008 |
| JP | 2014-150861 A | 8/2014 |
| WO | 2009/073898 A2 | 6/2009 |

OTHER PUBLICATIONS

International Search Report issued in PCT/JP2018/019809; dated Jul. 24, 2018.

Office Action issued in JP 2018-557963; mailed by the Japanese Patent Office dated Apr. 15, 2019.

Office Action issued in JP 2018-557963; mailed by the Japanese Patent Office dated Jul. 16, 2019.

Office Action issued in JP 2018-557963; mailed by the Japanese Patent Office dated Aug. 13, 2019.

The extended European search report issued by the European Patent Office dated Apr. 6, 2020, which corresponds to European Patent Application No. 18806753.2-1126 and is related to U.S. Appl. No. 16/616,935.

An Office Action issued by the State Intellectual Property Office of the People's Republic of China dated Jul. 29, 2020, which corresponds to Chinese Patent Application No. CN 201880033284.0.

FIG.1
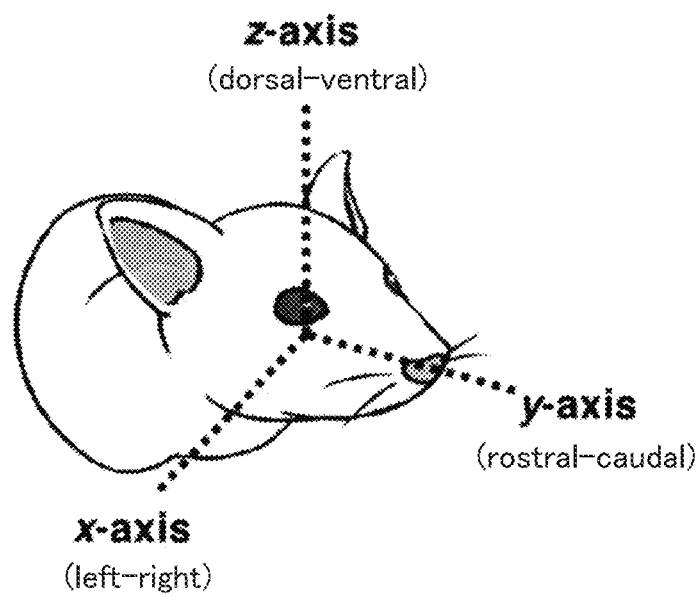
FIG.2A
Treadmill running
z-axis 
y-axis 
x-axis 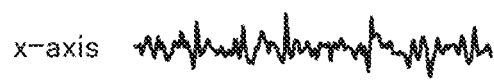

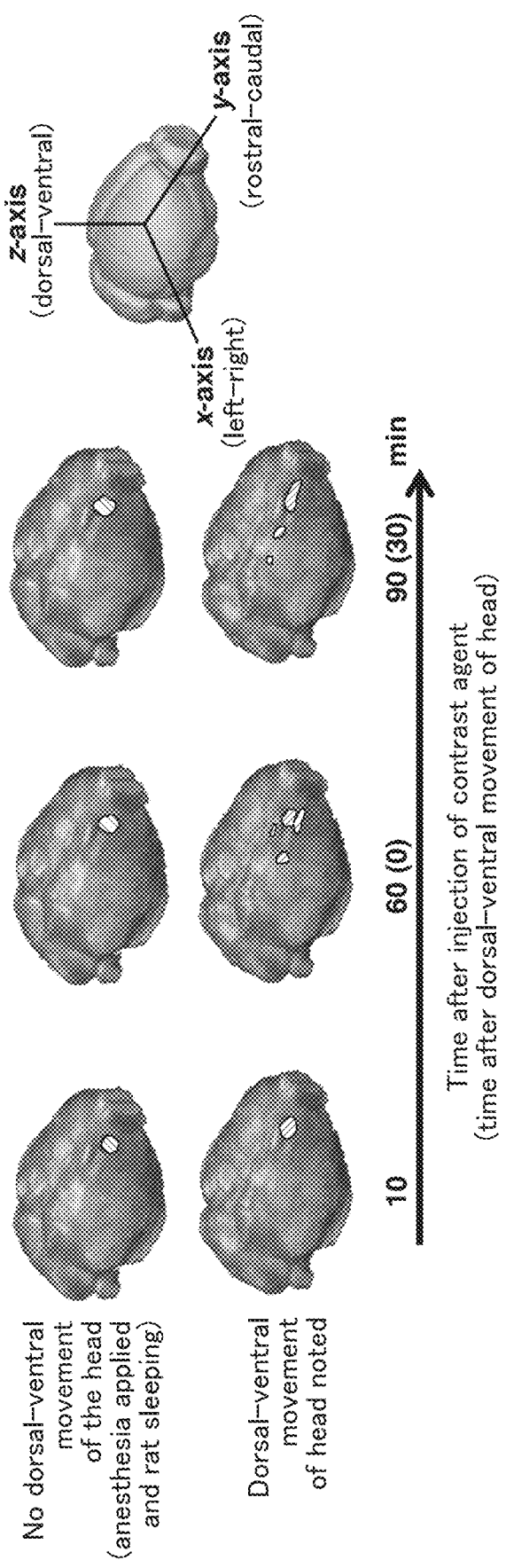

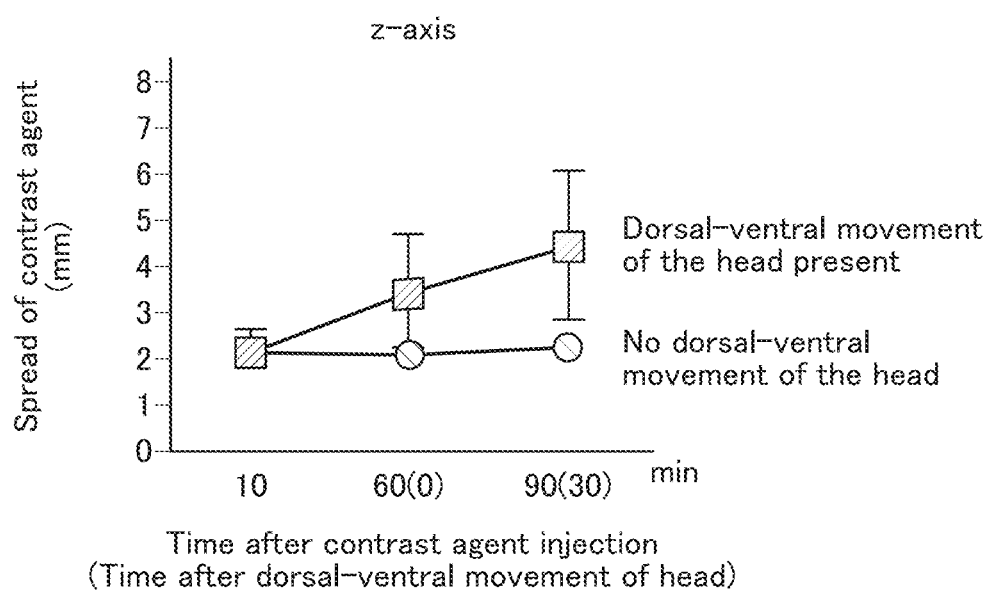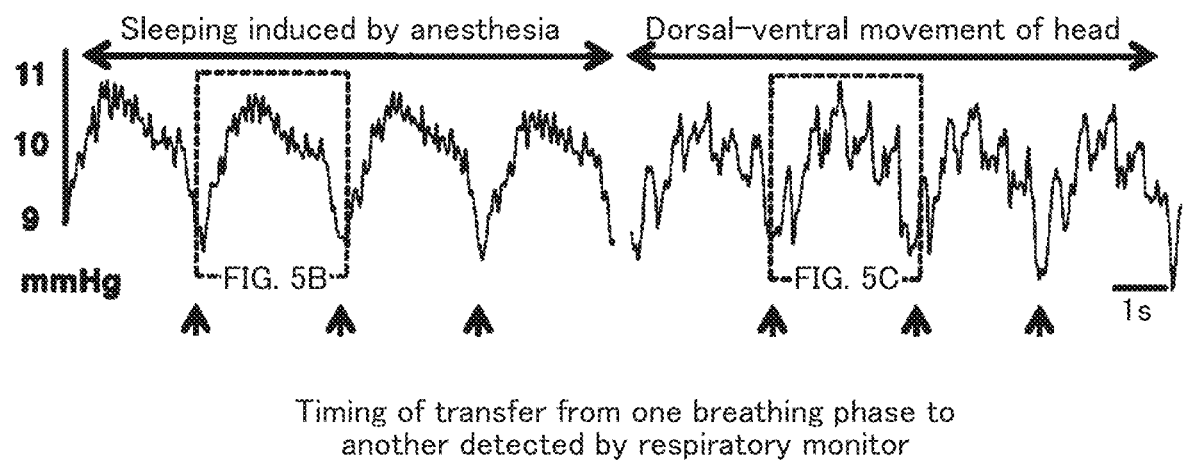

FIG.8

| Structure | Diameter (cm) | Wall shear stress (dyn/cm²) |
|---|---|---|
| Aorta | 1.0 | 12.0 |
| Large arteries | 0.3 | 10.4 |
| | 0.3 | 15.8 |
| | 0.34 | 16.4 |
| Small arteries | 0.1 | 18.6 |
| Terminal branches | 0.06 | 23.0 |
| Arteriole | 0.002 | 14.1 |
| Capillaries | 0.00055 | 20.8 |
| | 0.00053 | 26.1 |
| | 0.0007 | ~10 |
| Venule | 0.003 | 2.8 |
| Terminal branches | 0.15 | 2.0 |
| Small veins | 0.24 | 1.5 |
| Large veins | 0.6 | 1.4 |
| Vena cava | 1.25 | 6.3 |

1 Pa = 10 dyn/cm²

FIG.22
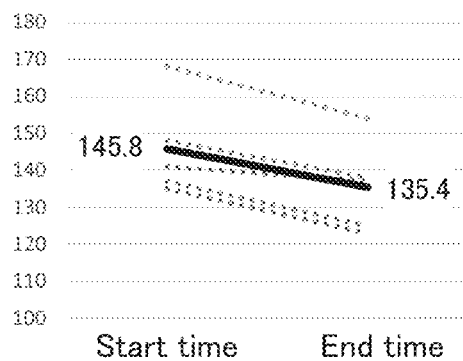
Systolic blood pressure (mmHg)
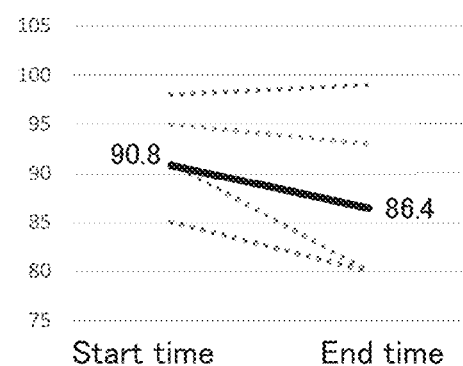
Diastolic blood pressure (mmHg)
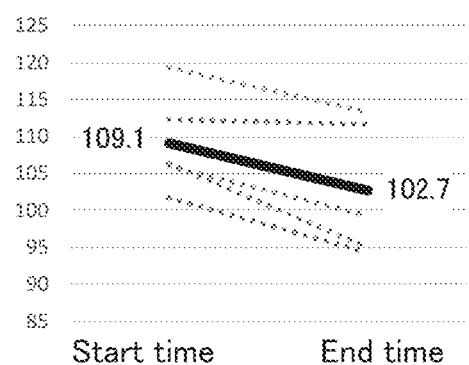
Average blood pressure (mmHg)
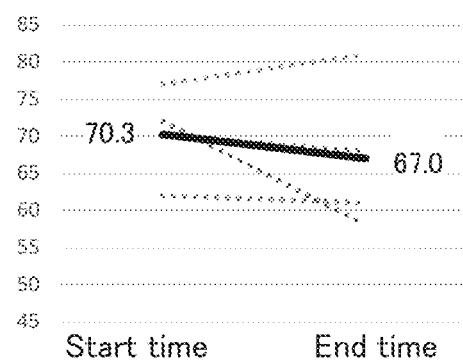
Heart rate (beats/min)

HEALTH PROMOTING APPARATUS

TECHNICAL FIELD

The present invention relates to a health promoting apparatus to benefit health of a user based on moderate exercise.

BACKGROUND ART

With many people getting increasingly and easily stressed, a living environment where they can relax and relieve their stress has become more and more desirable. To this end, "moderate exercise" has been recommended to relieve their stress in order to maintain and promote better health.

However, because the extent to which exercise can be considered "moderate" has yet to be defined, there is a possibility that those who exercise may be doing so in excess. This would be rather detrimental to their health.

Although various health promoting apparatuses have been recently developed to apply physical movement to a particular part or the entire body of the user, most are founded on user review such as "relief of stiff shoulder" and "stimulation of pressure point", without taking medicinal factors into consideration.

SUMMARY OF INVENTION

Technical Problem

In the conventional apparatuses as mentioned above, there is a problem in the inability to improve various disease or fatigue conditions based on the physiological benefits of "moderate exercise".

The present invention has been made in view of solving this problem, and an object thereof is to provide a health promoting apparatus capable of improving various disease or fatigue conditions based on medical factors underlying moderate exercise derived from scientific experimentation.

Solution to Technical Problem

In order to achieve the above object, according to one aspect of the present invention, there is provided a health promoting apparatus to benefit health of a user based on medical factors underlying moderate exercise, the apparatus includes: an oscillation generator configured to oscillate a head of the user in a vertical direction or an anteroposterior direction; and an oscillation controller connected to the oscillation generator, and configured to control an oscillation generated by the oscillation generator, wherein the oscillation controller is configured: to control the oscillation generator to apply shear stress to cells in the brain of the user by moving interstitial fluid in the brain, in order to promote the health of the user: to set a frequency of the oscillation from 1 to 3 Hz, and to accelerate the head of the user from ±0.3 to 2.0×g.

In the health promoting apparatus of the present invention, the oscillation controller may be configured to set an amplitude (stroke) of the oscillation in the vertical direction to equal to or less than 8 cm.

In the health promoting apparatus of the present invention, the oscillation controller may be configured to set duration of the oscillation from 10 to 60 minutes or until the user falls asleep.

In the health promoting apparatus of the present invention, the apparatus may be configured to oscillate the head of the user in the vertical direction while the user is seated.

In the health promoting apparatus of the present invention, the apparatus may further include: a seat part on which the user sits, and to which the oscillation is applied by the oscillation generator; a backrest part which supports a back of the user; and a headrest part which supports the head of the user, and the apparatus may be configured to oscillate the head of the user in the vertical direction, in such a state that the head is supported by the headrest part.

Effect of Invention

Utilizing the health promoting apparatus of the presented invention, it is possible to achieve an improvement of various disease or fatigue conditions by applying an oscillation to a head in a vertical or anteroposterior direction, to mimic the physiological effects of moderate exercise elucidated by scientific experimentation.

BRIEF DESCRIPTION OF DRAWINGS

FIG. 1 is a schematic diagram to explain a principle of a health promoting apparatus of the present invention.

FIG. 2A shows measurement results of acceleration generated at the head of a rat during treadmill running.

FIG. 3 shows an interstitial fluid flow in the cerebral cortex of a rat caused by passive head motion using contrast-enhanced MRI.

FIG. 4C shows quantification of spreading of the contrast agent in the cerebral cortex of a rat caused by passive head motion in the z-axis direction.

FIG. 5A shows intracerebral pressure of a rat, with and without exposure to passive head motion.

FIG. 8 shows a magnitude of a shear stress applied to a blood vessel wall by a blood flow.

FIG. 22 is an explanatory diagram of effects by a first embodiment in the present invention.

DESCRIPTION OF EMBODIMENTS

With reference to the accompanying drawings, a health promoting apparatus according to embodiments of the present invention will now be described.

Prior to the explanation of the health promoting apparatus in the present invention, the physiological benefits of moderate exercise elucidated by the inventors will be explained.

The inventors of the presented invention measured acceleration generated in the heads of rats in three axial directions (i.e., x-axis, y-axis and z-axis) as shown in FIG. 1. Accelerations were obtained during treadmill running, as shown in FIG. 2A, and upon exposure to passive head motion, as shown in FIG. 2B.

As shown in FIG. 2A, significant acceleration of the heads of the rats were measured not only in the z-axis (vertical direction) but also in the x- and y-axis during treadmill running.

Figure 2B:
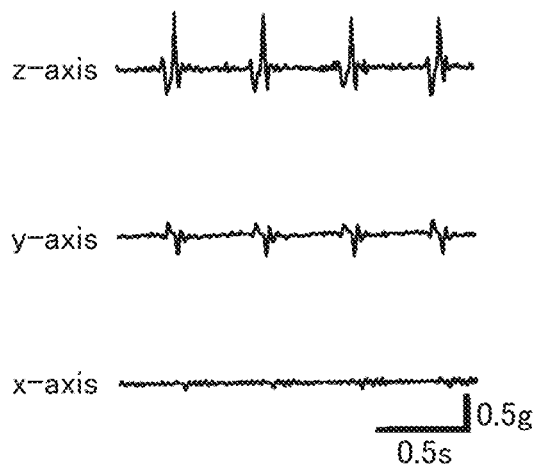
FIG. 2B shows measurement results of acceleration generated at the head of a rat during passive head motion.

On the other hand, as shown in FIG. 2B, the acceleration of the head of the rats were measured only in the z-axis (vertical direction), while little acceleration was measured in the x-axis and the y-axis, upon exposure to passive head motion.

Taken together, the acceleration of the head of the rats during treadmill running and upon exposure to passive head motion were only the same in the vertical direction (z-axis). The results suggest that the direction of the acceleration is an important parameter to measure moderate exercise.

Figure 4A:
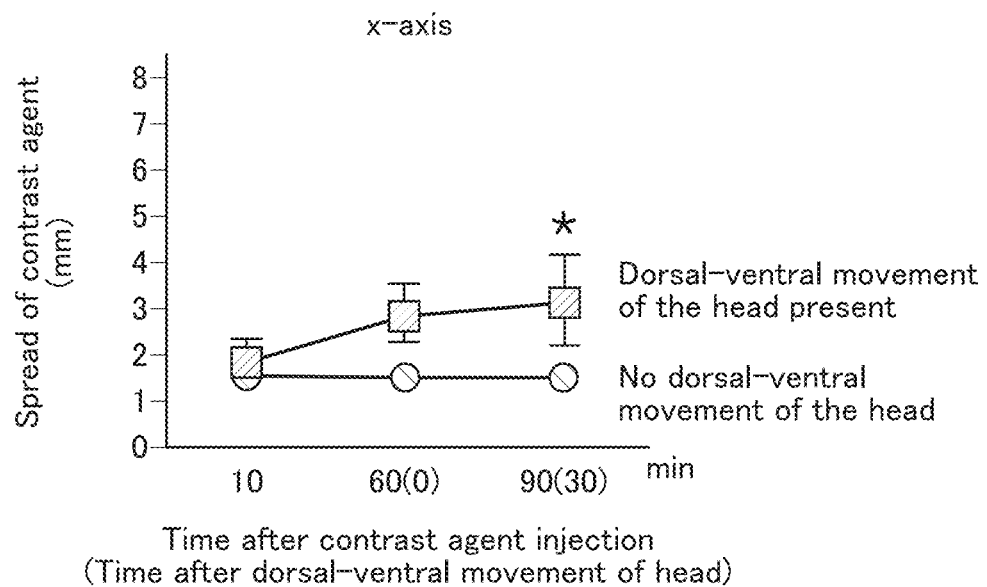
FIG. 4A shows quantification of spreading of the contrast agent in the cerebral cortex of a rat caused by passive head motion in the x-axis direction.
Figure 4B:
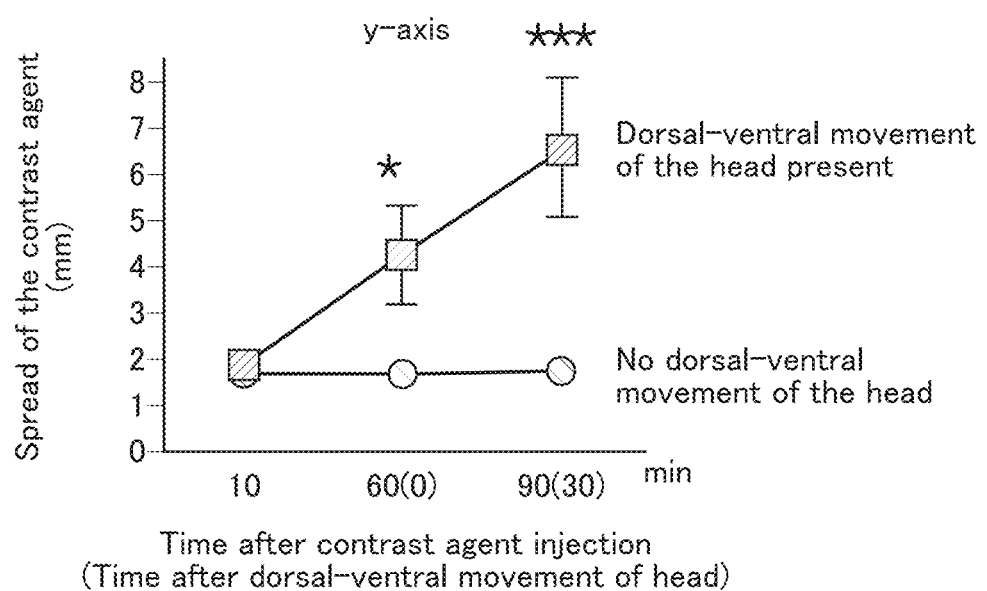
FIG. 4B shows quantification of spreading of the contrast agent in the cerebral cortex of a rat caused by passive head motion in the y-axis direction.

Contrast-enhanced MRI comparing rats exposed to passive head motion to those unexposed revealed that passive head motion causes interstitial fluid flow in the x-(horizontal) and y-(anteroposterior) axes, as shown in FIG. 3 and quantified in FIG. 4A, 4B, 4C. These results suggest that passive head motion enhances interstitial fluid flow along defined axes.

Figure 5B:
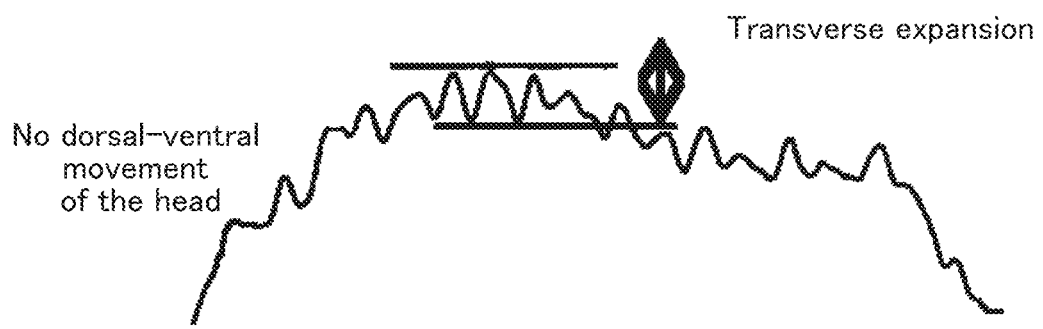
FIG. 5B is an enlarged view of a dashed area in FIG. 5A during absence of passive head motion.
Figure 5C:
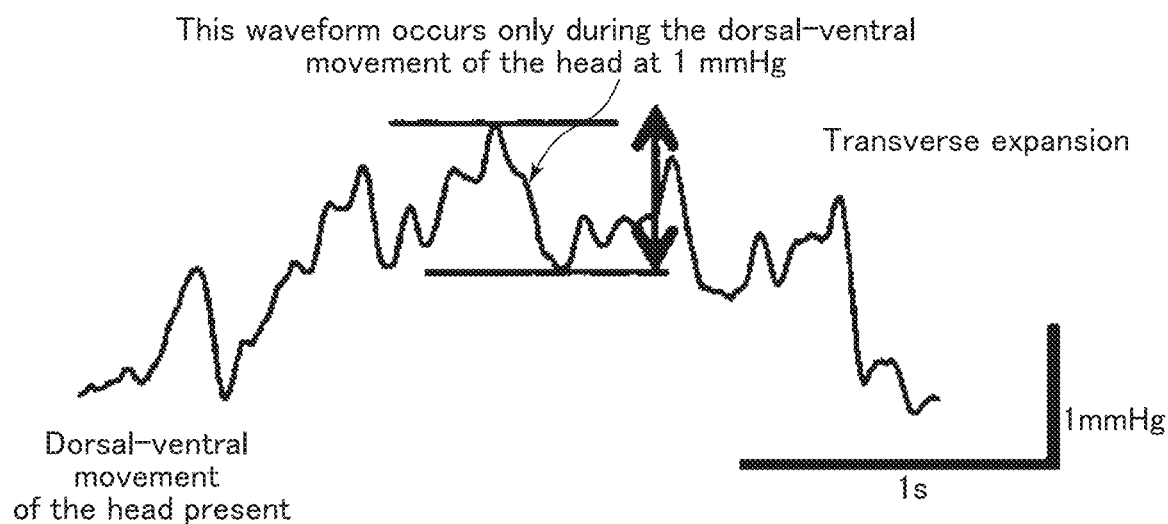
FIG. 5C is an enlarged view of a dashed area in FIG. 5A during exposure to passive head motion.
Figure 6:
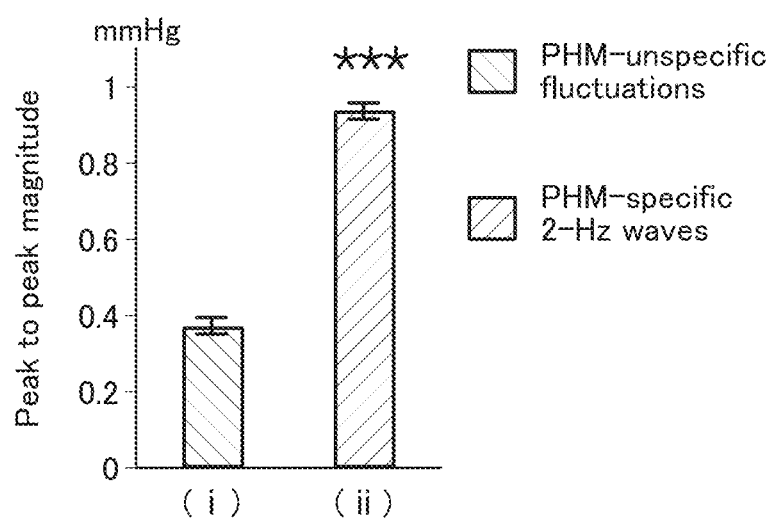
FIG. 6 shows consolidated data of pressure changes in the brain of rats without exposure to passive head motion (shown in (i)), and during exposure to passive head motion (shown in (ii)).

FIGS. 5A, 5B and 5C are diagrams showing pressure changes in the brains of the rats upon exposure to passive head motion. FIG. 5A shows the time points at which the transition from inhalation to exhalation is detected by the respiration monitor while the rat is anesthetized both with and without exposure to passive head motion. FIG. 5B is the enlarged view of the dashed area in FIG. 5A without exposure to passive head motion, and FIG. 5C is the enlarged view of the dashed area in FIG. 5A during exposure to passive head motion. Specifically, FIG. 5C shows the pressure change of 1 mmHg (1% of the average blood pressure) in the cerebral cortex. Experimental replicates of results shown in FIGS. 5A, 5B, and 5c are consolidated in FIG. 6. This supports the notion that passive head motion brings about changes in pressure distribution, thereby driving local interstitial fluid flow in the rat's brain. Our simulative calculation suggests that passive head motion subjected the cells to interstitial fluid flow-derived shear stress with the average magnitude of 0.6-3.6 Pa.

Figure 7A:
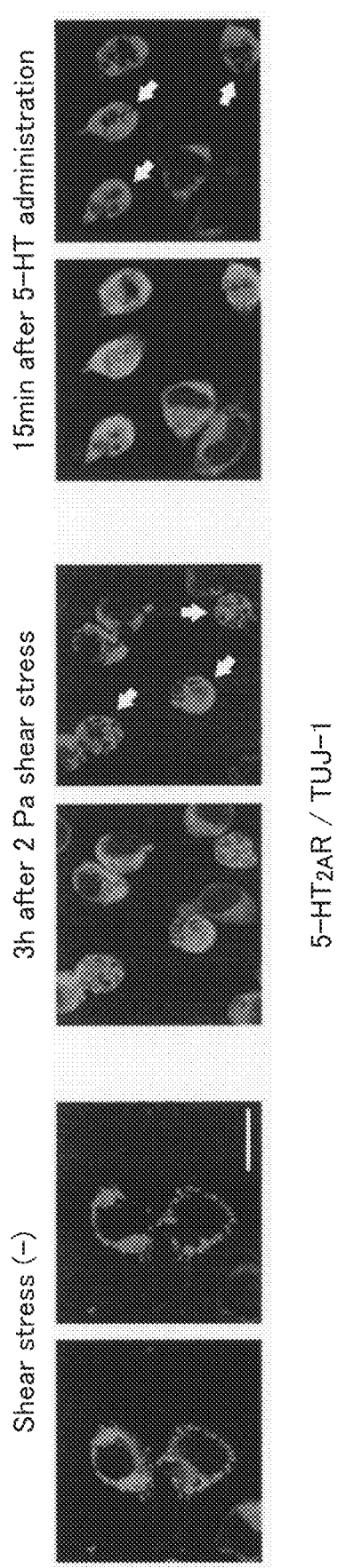
FIG. 7A shows a translocation of serotonin receptors from surface to cytosol of neuronal cells of neuronal cells by application of shear stress, which is caused by an interstitial fluid movement.
Figure 7B:
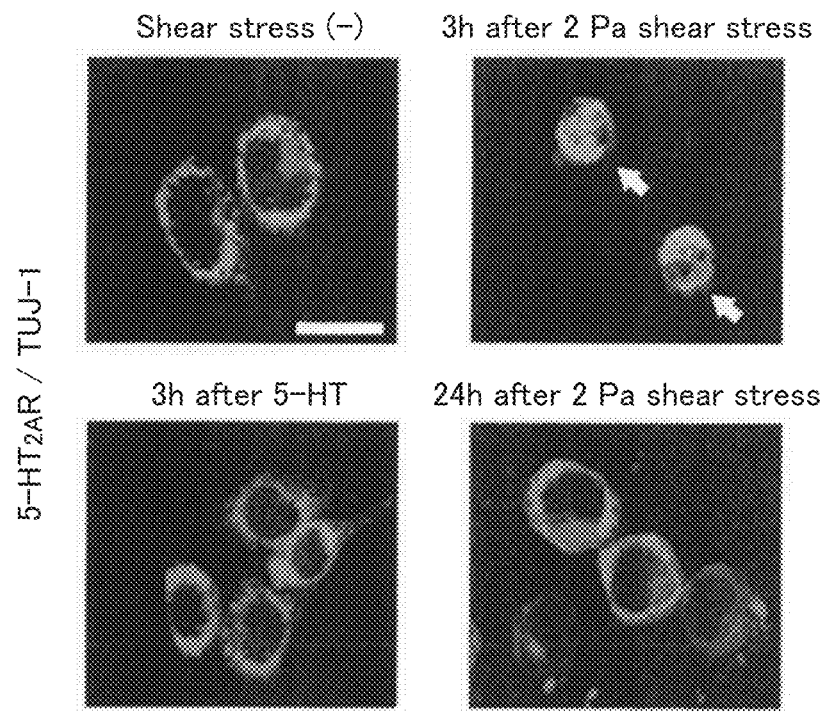
FIG. 7B shows a translocation of serotonin receptors from surface to cytosol of neuronal cells of neuronal cells by application of shear stress, which is caused by an interstitial fluid movement.
Figure 7C:
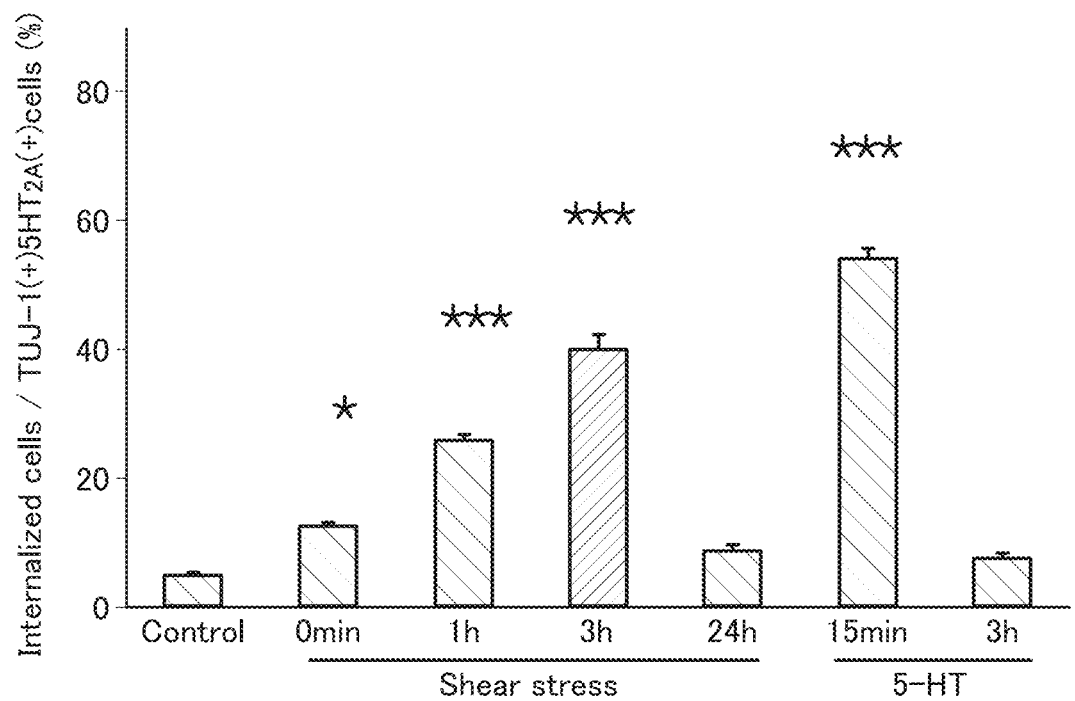
FIG. 7C shows a quantification of a translocation of serotonin receptors from surface to cytosol of neuronal cells by application of shear stress, which is caused by an interstitial fluid movement.

The inventors then exposed cultured neuronal cells to fluid sheer stress with the average magnitude of 2 Pa to investigate the effects of interstitial fluid flow-derived shear stress that both treadmill running and passive head motion cause. As shown in FIGS. 7A, 7B, 7C, results indicate rapid internalization of a subtype of serotonin receptor, $5\text{-}HT_{2A}$ receptor, signifying the suppression of serotonin signaling.

Taken together, the inventors concluded local interstitial fluid movement in the brain caused by vertical acceleration of the head to be, at least one of, the underlying factors of the beneficial effects of physical exercise. The application of vertical acceleration to the head can improve the hypnagogic disorder and has an effect on the following diseases and disorders other than the sleep induction.
(a) Hypertension (effect on the central control region of the blood pressure in the medulla oblongata)
(b) Diabetes (effect on the carbohydrate metabolism control region in the hypothalamus)
(c) Dementia (effect on the hippocampus)
(d) Depression and schizophrenia (effect on the cerebral cortex)

The effects on (a) and (c) are based on the data from animal experiments, and the effect on (b) is based on the conventional knowledges of the diabetes. The effect on (d) is based on the aforementioned data regarding the response of serotonin signalling after interstitial fluid flow-derived sheer stress in neuronal cells.

In the present invention, a vertical acceleration is applied to the head to cause an interstitial fluid movement, based on the medical factor underlying moderate exercise. By doing so, the present invention applies the shear stress to cells exposed to the interstitial fluid and can promote the health of the user.

In order to embody the the health promoting apparatus of the present invention, it is necessary to make a machine that can generate acceleration in the z-axis (vertical direction) of the user's head.

Figure 9:
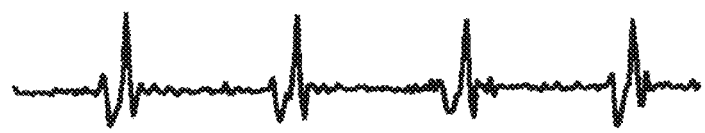
FIG. 9 shows an example of an impulse-shaped acceleration generated by a health promoting apparatus of the present invention.

The acceleration may be the impulse-shaped, as shown in FIG. 9, or sinewave-shaped acceleration (not shown). As long as movement of the interstitial fluid or pressure change in the brain is ensured, various shapes of the acceleration can be generated.

Figure 10:
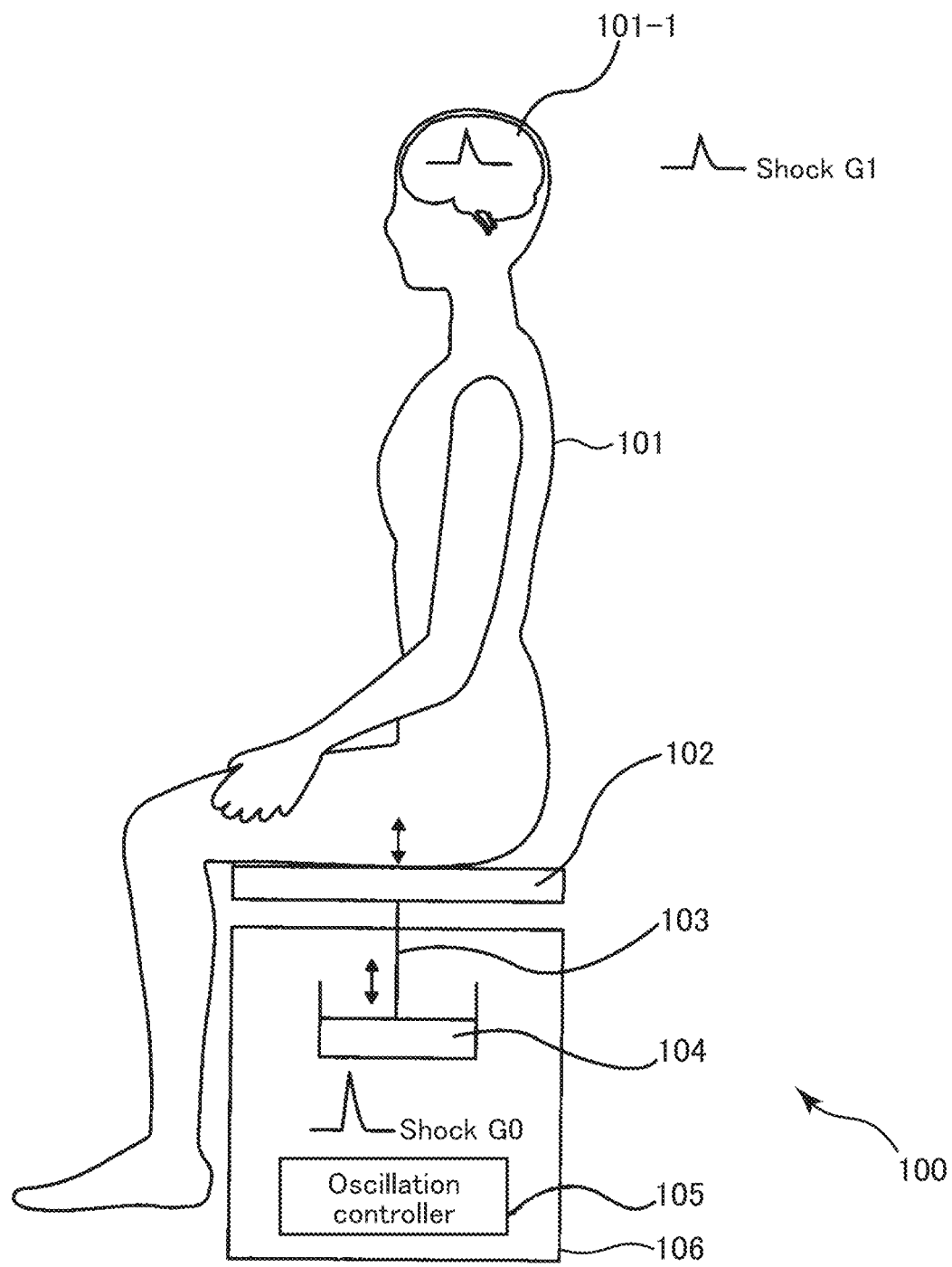
FIG. 10 is a schematic configuration diagram showing a health promoting apparatus using a vertical movement in a seated position, in a first embodiment of the present invention.

FIG. 10 is a schematic configuration diagram showing the health promoting apparatus in a first embodiment which promotes the health of the user base on the above medical factor caused by the moderate exercise. The health promoting apparatus is configured to oscillate the head of the user in the seated position, in the vertical direction.

The health promoting apparatus 100 shown in FIG. 10 includes: a seat part 102 having a seating surface on which the user 101 sits; a push rod 103 connected to the seat part 102; an oscillation generator (actuator) 104 connected to the push rod 103, and configured to apply the oscillation to the seat part 102 via the push rod 103: an oscillation controller 105 connected to the oscillation generator 104, and configured to control various dynamic characteristics of the oscillation generator 104: and a housing (storage box) 106 configured to house the seat part 102, the push rod 103, the oscillation generator 104 and the oscillation controller 105. The oscillation controller 105 is based on a well-known microcomputer, and includes at least one processor (corresponding to CPU (Central Processing Unit)) for executing a program, a memory composed of, e.g., a RAM (Random Access Memory) and a ROM (Read Only Memory) and capable of storing therein a program and data, and an input-output bus for inputting and outputting electric signals.

The seat part 102 is formed by a material which can easily fit to the buttocks of the user 101, and is connected to the oscillation generator 104 via the push rod 103.

The oscillation generator 104 has the mechanism for oscillating the seat part 102 by the predetermined specifications. The mechanism is explained later.

Figure 21:
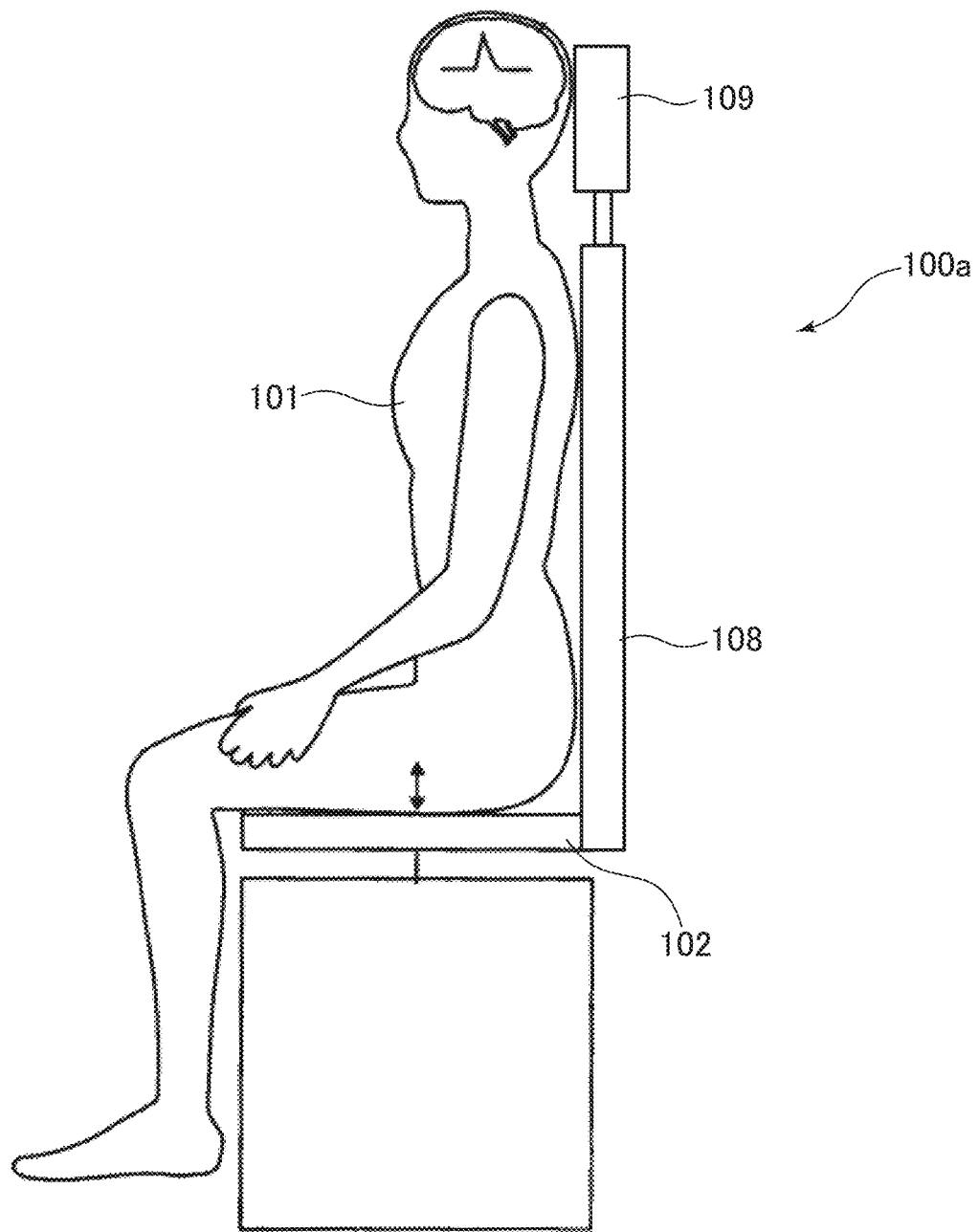
FIG. 21 is a schematic configuration diagram showing a health promoting apparatus in a modification of a first embodiment.

While only the seat part 102 is provided in the health promoting apparatus 100 shown in FIG. 10, as the part used when the user 101 sits, a backrest part 108 which supports the back of the user 101 may be provided in addition to the seat part 102, as depicted in FIG. 21 which shows a health promoting apparatus 100a in a modification of the first embodiment. Further, a headrest part 109 which supports the head of the user 101 may be provided in addition to the backrest part 108. As one example, as shown in FIG. 21, the headrest part 109 is separately provided above the backrest part 108. As another example, the backrest part 108 may be extended to the head positon of the user 101, and the headrest part 109 may be provided on the backrest part 108. In this case, the oscillation can be generated in such a state that the head of the user 101 is supported by the headrest part 109, and thereby it becomes possible to stabilize the acceleration (impact) applied to the head by the oscillation.

Figure 11:
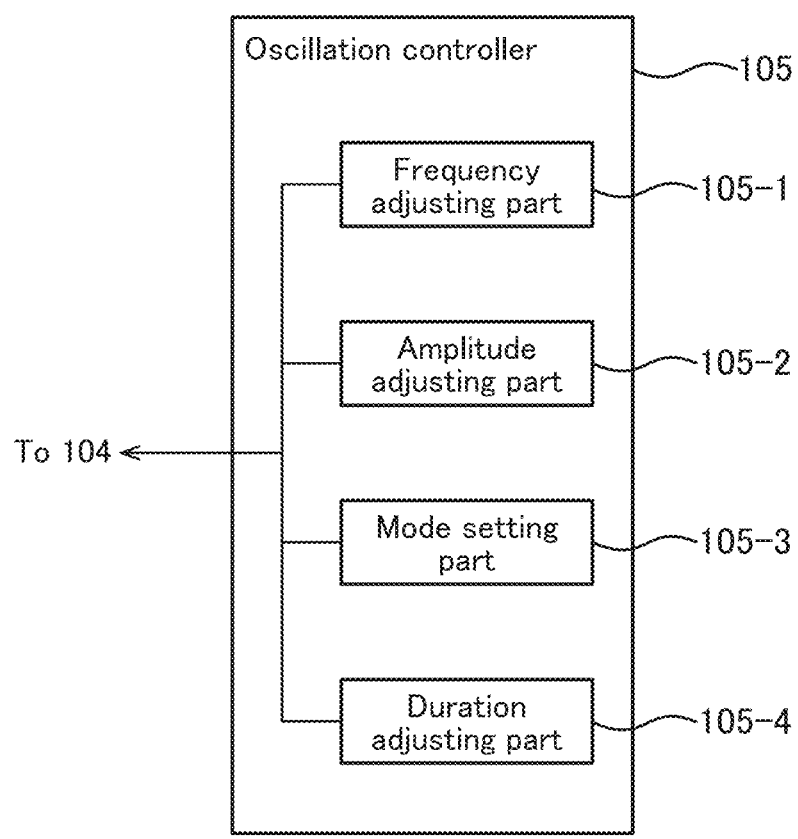
FIG. 11 is a schematic configuration diagram showing an example of an oscillation controller in the health promoting apparatus shown in FIG. 10.

FIG. 11 is a schematic configuration diagram showing an example of the oscillation controller 105 in FIG. 10.

The oscillation controller 105 comprises various parts 105-1 to 105-4 which are explained in detail later, and said parts 105-1 to 105-4 are configured to control the operation of the oscillation generator 104 so that it can generate the oscillation with the following specifications.

(1) A frequency adjusting part 105-1 is configured to control the frequency of the oscillation generated by the oscillation generator 104, and to set the frequency from 1 to 3 Hz (1 to 3 times per second, in other words 60 to 180 times per minute). This frequency corresponds to the normal heart rate (pulse). Furthermore, this frequency corresponds to the average walking step rate of healthy adults. When the number of steps required to achieve the normal walking pace of 5 to 6 km/h was measured, it was concluded that the average walking step rate was 2 steps per second.

(2) An amplitude adjusting part 105-2 is configured to control the amplitude (stroke) of the oscillation generated by the oscillation generator 104, and to set the amplitude (width (magnitude) of the vertical movement), to equal to or less than 8 cm. The value of the amplitude is based on the common research which reports that the width (magnitude) of the vertical movement of the head during the normal walking of the healthy adults is about 5 cm.

(3) A mode setting part 105-3 is configured to control the mode of the movement of the oscillation generated by the oscillation generator 104, and to control the acceleration (impact) applied to the head, to ±0.3 to 2.0×g (i.e., 0.3 to 2.0 times the amount of the gravitational acceleration (9.8 m/s$^2$)). The value of the acceleration is based on the common research which reports that acceleration applied to the head during the normal walking of the healthy adults is about ±0.6×g. For example, as derived from experiments, the vertical acceleration generated in the head when walking at 4 km/h is 0.5×g, the vertical acceleration generated in the head when walking at 5 km/h is 0.6×g, the vertical acceleration generated in the head when walking at 6 km/h is 0.7×g, the vertical acceleration generated in the head when walking at 7 km/h (brisk walking) is 1.0×g, the vertical acceleration generated in the head when running at 8 km/h is 1.5×g, and the vertical acceleration generated in the head when running at 9 km/h is 1.8×g. According to the experiments using rats, it turns out that 1×g of the vertical acceleration of the head is effective.

Not only impulse-shaped acceleration (impact) but also the sinewave-shaped acceleration may be applied to the mode of the vertical movement. As long as the resulting movement of the interstitial fluid or the pressure change in the brain is ensured to be beneficial upon consideration of its use, various shapes of the acceleration may be applied to the mode of the vertical movement.

(4) A duration adjusting part 105-4 is configured to control the duration of the oscillation generated by the oscillation generator 104, and to allow the duration to be set to 10-60 minutes or until the user falls asleep. The duration is based on the time (up to about 60 minutes) that is commonly recommended for moderate exercise and the duration (30 minutes) that is used for the vertical movement of the head in the animal experiments.

Figure 12:
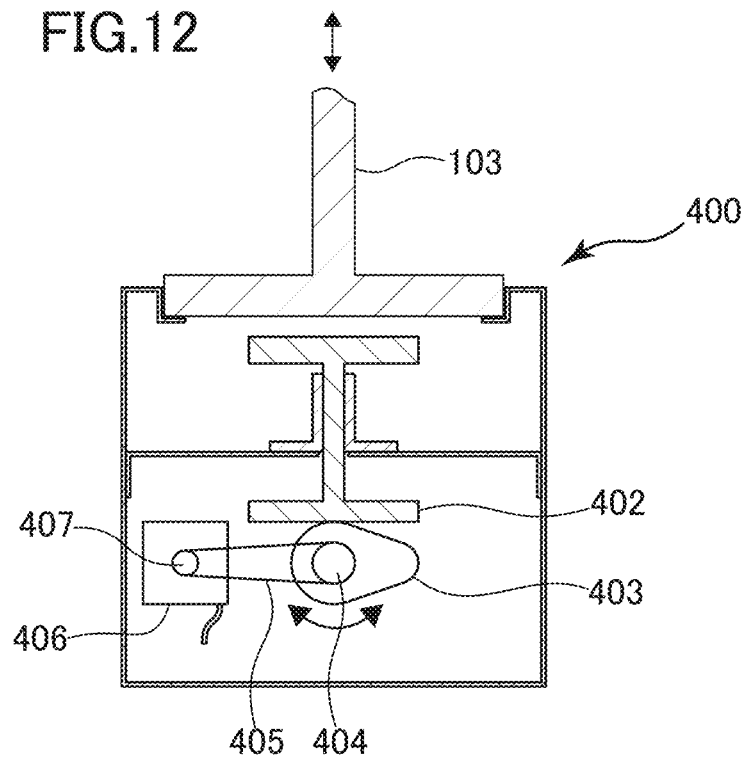
FIG. 12 is a diagram illustrating movements of a cam-type oscillation generator in the health promoting apparatus shown in FIG. 10.
Figure 13:
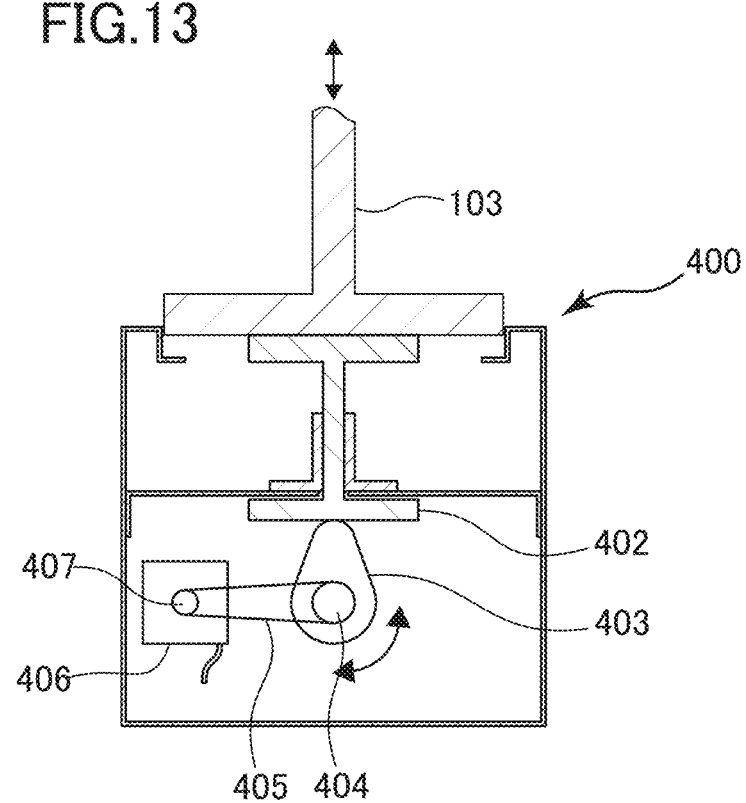
FIG. 13 is another diagram illustrating movements of the cam-type oscillation generator shown in FIG. 12.

FIGS. 12 and 13 are diagrams for explaining an operation of a cam-type oscillation generator as the above-mentioned oscillation generator 104 included in the health promoting apparatus 100 shown in FIG. 10.

The cam-type oscillation generator 400 shown in FIGS. 12 and 13 includes a tappet 402, a cam 403, a cam-side pulley 404, a belt 405, a motor 406, and a motor-side pulley 407.

As shown in FIGS. 12 and 13, the cam-type oscillation generator 400 is configured such that when the motor 406 rotates, the cam 403 rotates via the motor-side pulley 407, the belt 405 and the cam-side pulley 404, thereby moving the tappet 402 in the vertical direction. When that occurs, the push rod 103 moves in the vertical direction so that the seat part 102 oscillates in the vertical direction (z-axis direction).

Figure 14:
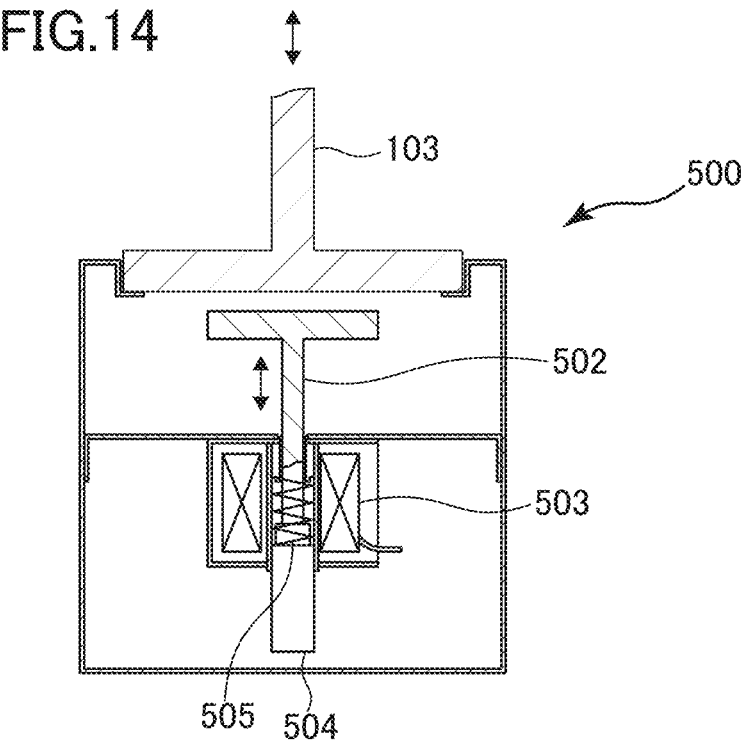
FIG. 14 is a diagram illustrating movements of a solenoid-type oscillation generator in the health promoting apparatus shown in FIG. 10.
Figure 15:
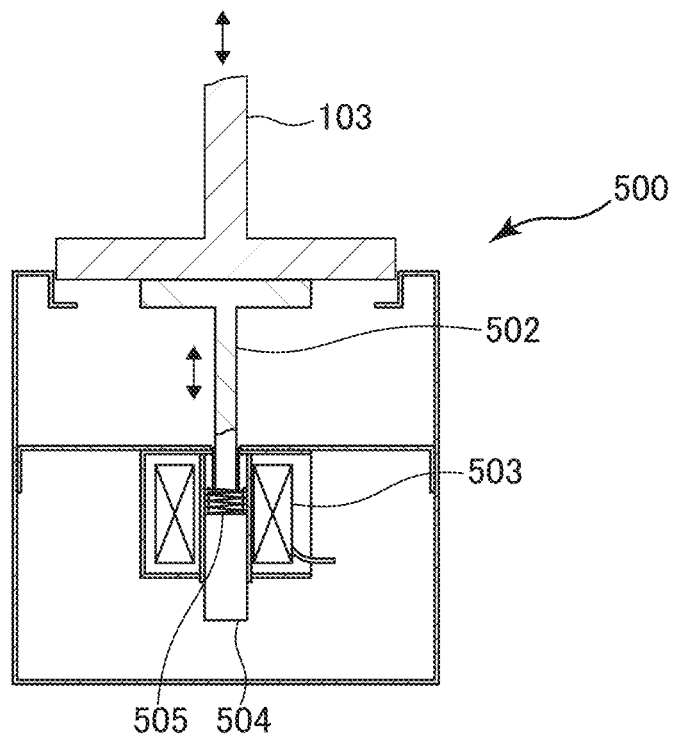
FIG. 15 is another diagram illustrating the solenoid-type oscillation generator shown in FIG. 14.

FIGS. 14 and 15 are diagrams for explaining an operation of a solenoid-type oscillation generator as the above-mentioned oscillation generator 104 included in the health promoting apparatus 100 shown in FIG. 10.

The solenoid-type oscillation generator 500 shown in FIGS. 14 and 15 includes a plunger 502, an electromagnet 503, a magnet 504, and a spring 505.

As shown in FIGS. 14 and 15, the solenoid-type oscillation generator 500 is configured such that, when the electric power is supplied to the electromagnet 503, the magnet 504 moves upward and the plunger 502 pushes the push rod 103 upward. Then, when the electric power supplied to the electromagnet 503 stops, the magnet 504 moved downward by the spring 505 and the push rod 103 returns in the downward direction. Repetition of the above movements causes the push rod 103 to move in the vertical direction, causing the seat part 102 to oscillate in the vertical direction (z-axis direction).

Next, the operation of the health promoting apparatus 100 using the vertical movement in the seated position shown in FIGS. 10-15 is explained.

The posture of user 101 when using the health promoting apparatus 100 is the "seated position" as shown in FIG. 10. The seat part 102 is oscillated in the vertical direction (z-axis direction) by the above-mentioned mechanism causing the generation of "acceleration" in the vertical direction in the head 101-1 of user 101.

Further, when the user 101 uses the health promoting apparatus 100, "acceleration" in the vertical direction is generated in the abdomen and spine (thoracic spine and lumbar spine) of the user 101.

Then, the "acceleration" generated in the abdomen and spine during walking and running is mainly that which also moves in the vertical direction. Therefore, by using the health promoting apparatus 100, from the viewpoint of "acceleration", "the state when walking and running" is replicated in the case of user 101.

At the time of filing the present application, the inventors could confirm only the effectiveness of the vertical "acceleration" of the head 101-1 of the user 101 based on animal experiments. Therefore, the health promoting apparatus 100 can be suggested as an apparatus whereby "vertical movement in the seated position" can generate "acceleration" in the head 101-1 of the user 101.

By "vertical movements in the seated position" with the health promoting apparatus 100 mentioned above, "acceleration" is generated not only in the head 101-1 of the user 101 but also the abdomen (including visceral fat and liver) and spine (thoracic spine and lumbar spine).

Further, considering the fact that "moderate exercise" is effective as a therapeutic measure towards metabolic syndrome and osteoporosis, the "vertical movement in the seated position" of the health promoting apparatus 100 may prove the use of the health promoting apparatus 100 effective in treating other associated diseases and disorders.

Furthermore, with "vertical movement while seated", the user 101 requires no special effort (e.g. maintaining a certain posture when using the apparatus); even if the user 101 falls asleep in the seated position, the acceleration can be generated in the head 101-1 of the user 101.

FIG. 22 shows an explanatory diagram of the effect of the health promoting apparatus 100 in the first embodiment of this invention. FIG. 22 presents (in order from the top) the systolic blood pressure, the diastolic blood pressure, the average systolic and the diastolic blood pressures, and the heart rate of the subject (user) of the health promoting apparatus 100. In FIG. 22, the dashed lines represent the experimental results obtained from multiple subjects (five subjects), while the solid lines represent the average of the experimental results obtained from them.

Specifically, the results shown in FIG. 22 were obtained by the following experimental conditions:

Subjects (experiment participants): 5 adult men and women with systolic blood pressure of 135 mmHg or higher (people with relatively high blood pressure)

Frequency of oscillation of the health promoting apparatus: 2 Hz

Amplitude (stroke) of oscillation of the health promoting apparatus: 3 cm

Acceleration applied to the subject's head by oscillation of the health promoting apparatus: 1.0×g for subjects 1, 2, 4 and 5 and 0.6×g for subject 3

Use frequency, time, and duration of the health promoting apparatus: three times a week, 30 minutes per day, for 4 weeks Measurement of blood pressure: After remaining at rest for at least 5 min in the seated or supine position at a certain time in the morning (before lunch), the subjects measured their blood pressure and heart rate using an automated sphygmomanometer three times and recorded the average of the three measurements.

Blood pressure and heart rate just before the first use of the health promoting apparatus were recorded as the values at the start of the experiment. Blood pressure and heart rate immediately after the $12^{th}$ round of use of the health promoting apparatus were recorded as the values at the end of the experiment.

The following results were obtained when the experiments were performed based on the above conditions (FIG. 22):

Subject 1
  Start of the experiment: systolic blood pressure of 148 mmHg, diastolic blood pressure of 85 mmHg, and heart rate of 62 beats per minute
  End of the experiment: systolic blood pressure of 138 mmHg, diastolic blood pressure of 80 mmHg, and heart rate of 61 beats per minute Subject 2
  Start of the experiment: systolic blood pressure of 137 mmHg, diastolic blood pressure of 91 mmHg, and heart rate (not recorded)
  End of the experiment: systolic blood pressure of 125 mmHg, diastolic blood pressure of 80 mmHg, and heart rate of 69 beats per minute Subject 3
  Start of the experiment: systolic blood pressure of 168 mmHg, diastolic blood pressure of 95 mmHg, and heart rate of 70 beats per minute
  End of the experiment: systolic blood pressure of 154 mmHg, diastolic blood pressure of 93 mmHg, and heart rate of 68 beats per minute Subject 4
  Start of the experiment: systolic blood pressure of 141 mmHg, diastolic blood pressure of 98 mmHg, and heart rate of 77 beats per minute
  End of the experiment: systolic blood pressure of 137 mmHg, diastolic blood pressure of 99 mmHg, and heart rate of 81 beats per minute Subject 5
  Start of the experiment: systolic blood pressure of 135 mmHg, diastolic blood pressure of 85 mmHg, and heart rate of 72 beats per minute
  End of the experiment: systolic blood pressure of 123 mmHg, diastolic blood pressure of 80 mmHg, and heart rate of 58 beats per minute Thus, according to the results of the experiments, the systolic blood pressure and the average blood pressure of all five subjects decreased. Specifically, the systolic blood pressure decreased by an average of 10.4 mmHg, the diastolic blood pressure decreased by the average of 4.4 mmHg, and the average blood pressure of the systolic blood pressure and the diastolic blood pressure decreased by an average of 6.4 mmHg. Therefore, the above experiments have proven that the health promoting apparatus 100 in the first embodiment improves hypertension. Further, according to the findings with the health promoting apparatus 100 in the first embodiment, the heart rate of the four subjects decreased (for subject 2, the heart rate at the start of the experiment was not recorded). Specifically, the heart rate decreased by an average of 3.3 beats per minute.

Figure 16:
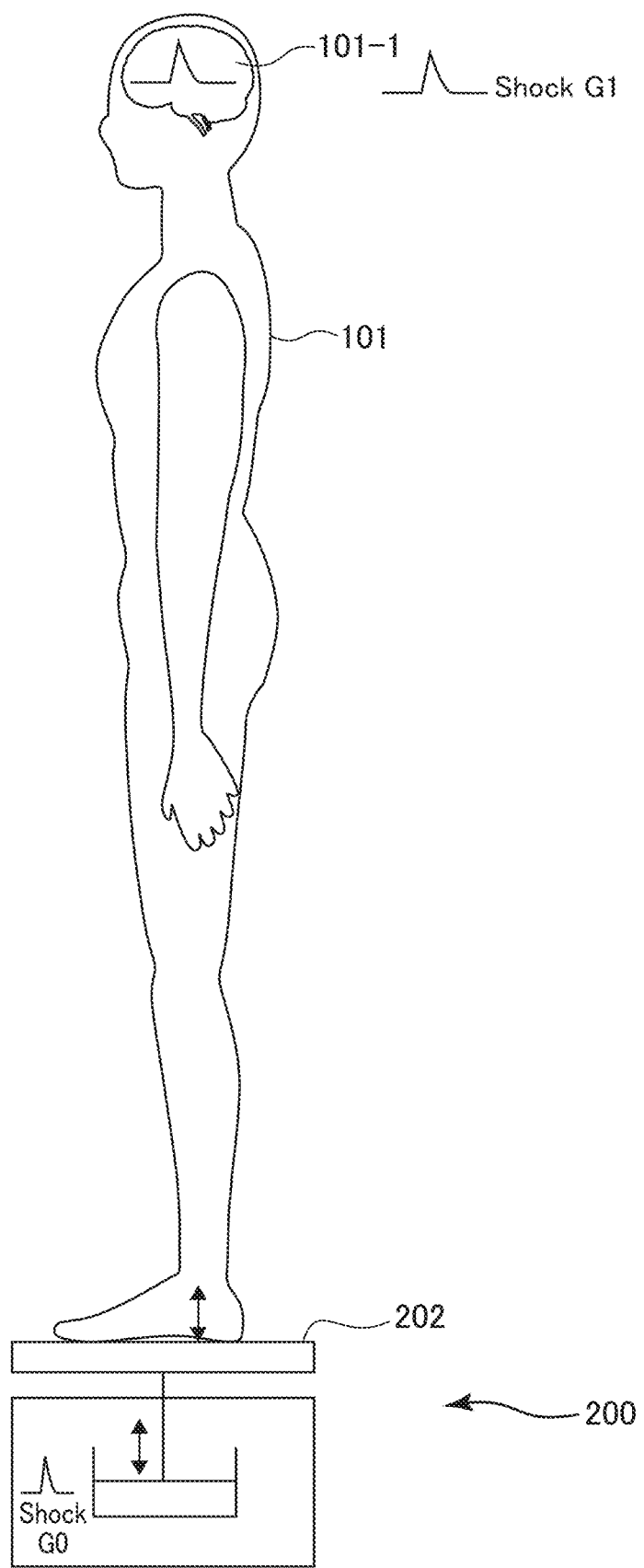
FIG. 16 is a schematic configuration diagram showing a health promoting apparatus using a vertical movement in an upright position, in a second embodiment of the present invention.

FIG. 16 shows a schematic configuration diagram of a health promoting apparatus in a second embodiment based on the present invention. The health promoting apparatus is configured to oscillate the head of the user in the vertical direction while the user is in the upright position.

The health promoting apparatus 200 shown in FIG. 16 uses the vertical movement in the upright position; thus, the posture of user 101 remains in the upright position. The only difference in the health promoting apparatus 200 is that it is equipped with a step part 202 with which the bottom of the foot of user 101 comes into contact instead of the seat part 102 in the first embodiment mentioned above. Hence, explanations of other parts in the configuration have been omitted.

The health promoting apparatus 200 that uses "vertical movement in the upright position" as shown in FIG. 16 is configured such that when the bottom of the foot of the user 101 contacts the step part 202, it moves vertically, causing the generation of "acceleration in the vertical direction" in the head 101-1 of the user 101.

With the health promoting apparatus 200, which uses "vertical movement in the upright position" as shown in FIG. 16, "vertical acceleration" is generated both in the abdomen and spine (thoracic spine and lumbar spine) as well as in the lower extremities. Therefore, from the viewpoint of "acceleration", the "state when walking and running" can be replicated with respect to the abdomen, the spine, and the lower extremities for the user 101 using the health promoting apparatus 200.

Thus, with the health promoting apparatus 200, which uses "vertical movement in the upright position", "acceleration" can be generated in the head 101-1 of the user 101 as well as in their abdomen (including visceral fat and liver), the spine (thoracic spine and lumbar spine), and the lower extremities.

Further, using the health promoting apparatus 200, which uses "vertical movement in the upright position", in addition to the diseases and disorders that can be addressed by the above-mentioned health promoting apparatus 100 that uses the vertical movement in the seated position, the same efficacy as that of "moderate exercise" is likely obtained on the bones of the lower extremities (i.e. femur, tibia, fibula) and skeletal muscle tissue of the lower extremities.

However, compared to the "vertical movement in the seated position type" of the apparatus, the user 101 must make special effort (e.g. at the time of use, a special posture [upright position] must be maintained).

Figure 17:
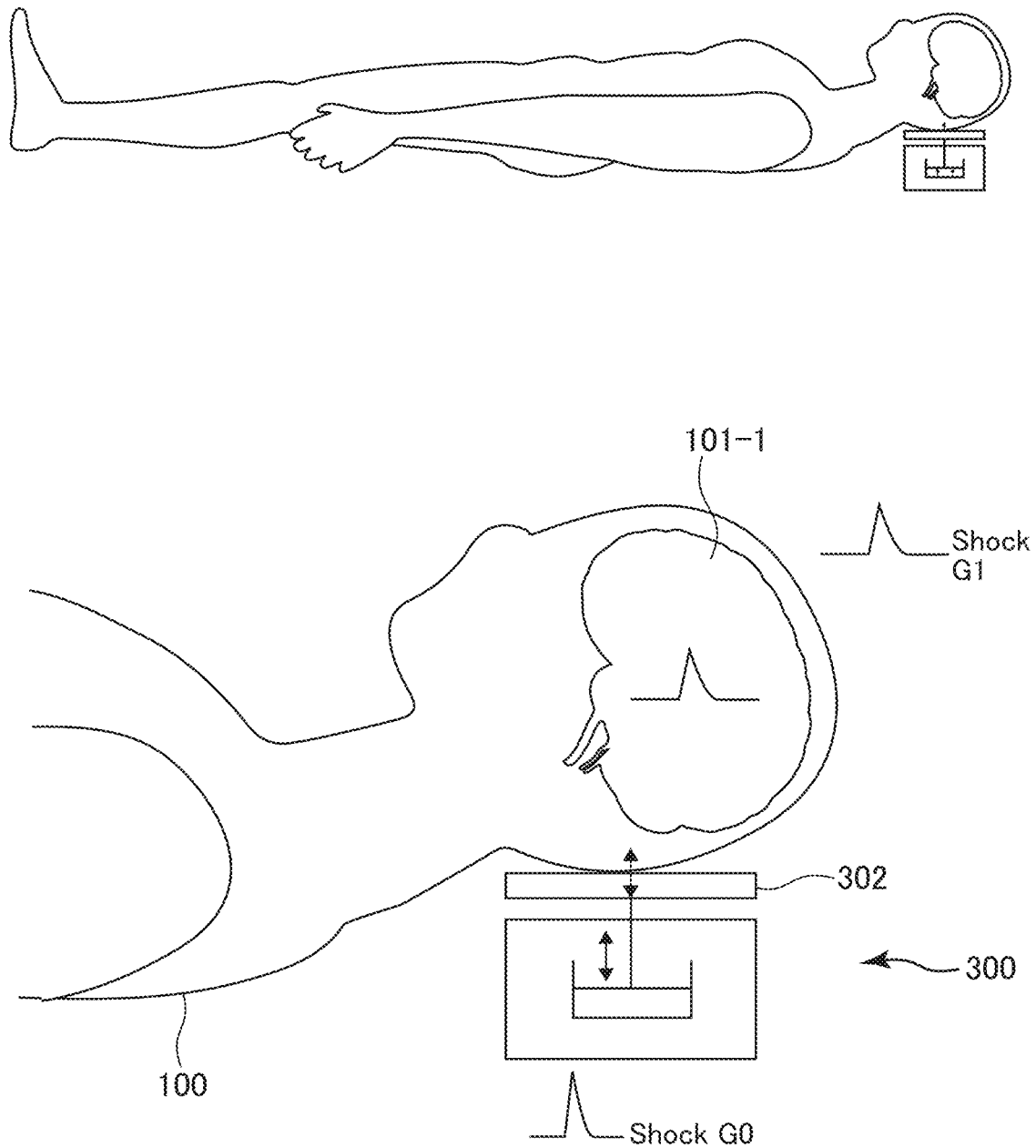
FIG. 17 is a schematic configuration diagram showing a health promoting apparatus using a vertical movement in a recumbent position, in a third embodiment of the present invention.
Figure 18:
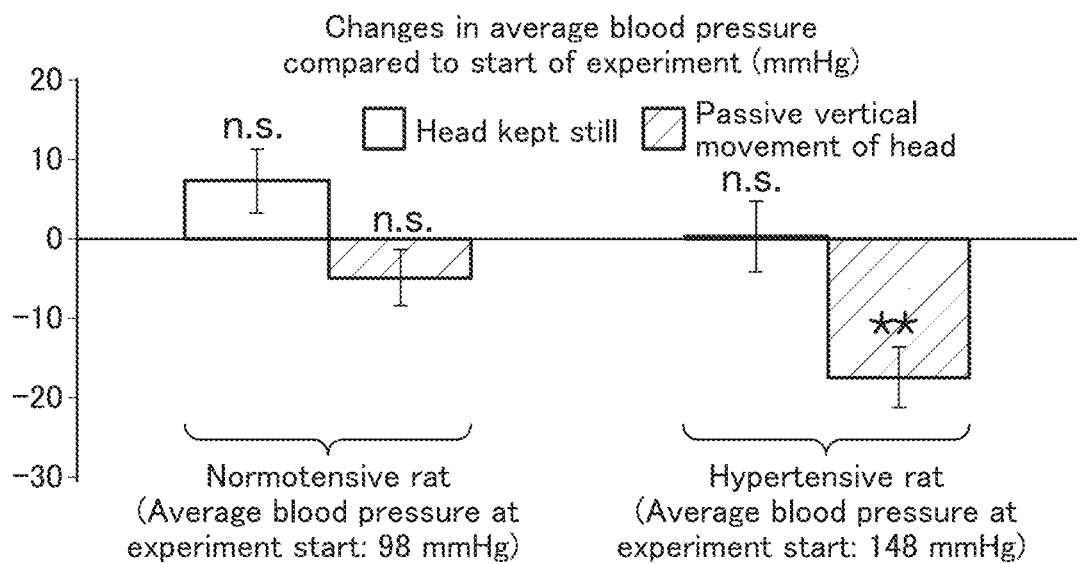
FIG. 18 shows a reduction in blood pressure of a hypertensive rat upon exposure to passive head motion.
Figure 19:
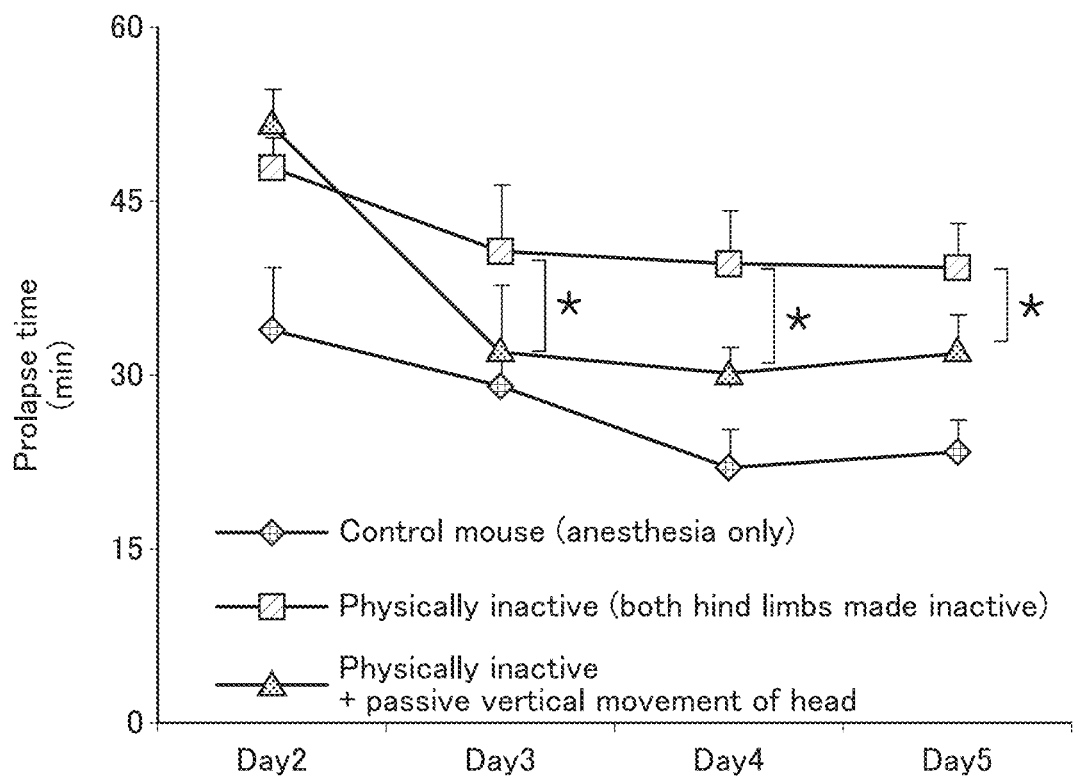
FIG. 19 shows results of Morris water maze test indicating a cognitive deficit (learning deficit) of a physically-inactive mouse, in which both hind limbs were immobilized, and a relief of the deficit after exposure to passive head motion.
Figure 20:
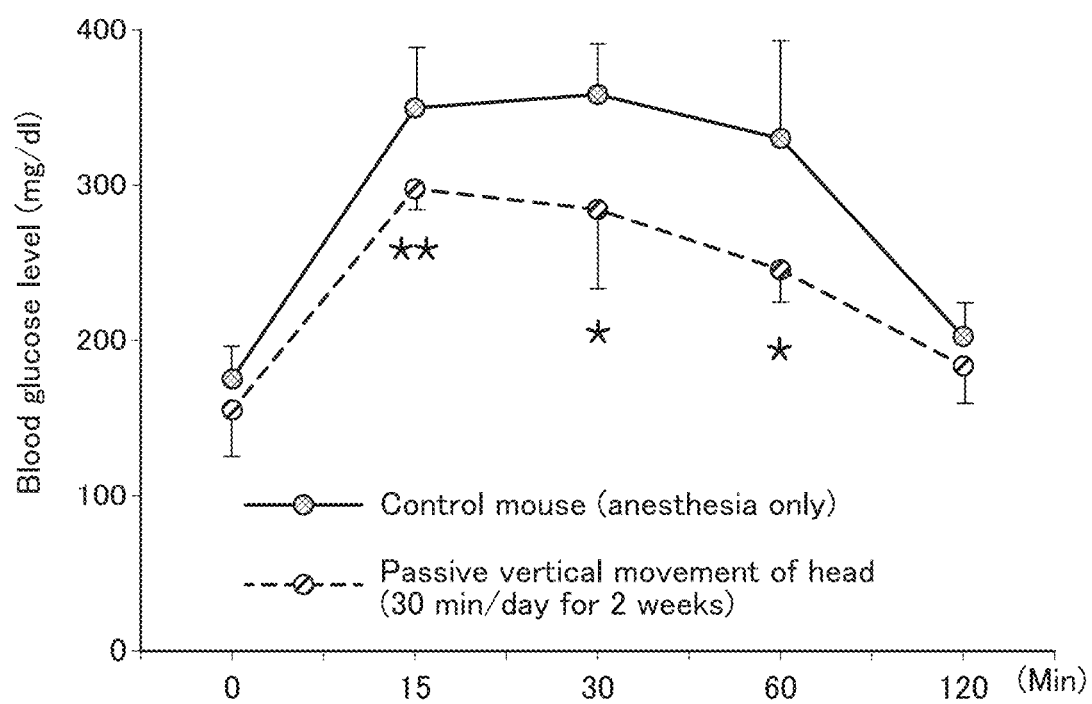
FIG. 20 shows an improvement of glucose tolerance of aged mice (32-week old) after exposure to passive head motion.

FIG. 17 shows a schematic configuration diagram of a health promoting apparatus in a third embodiment. This health promoting apparatus is configured to oscillate the head of the user in the vertical direction while the user is in the recumbent position.

The health promoting apparatus 300, shown in FIG. 17, oscillates the head in a vertical manner while the user is in the recumbent position. The health promoting apparatus 300 differs from the health promoting apparatus 200 in the second embodiment only in that the former includes a pillow part 302 with which the back of the head of user 101 comes into contact instead of the step part 202 mentioned above. Hence, explanations regarding other parts in the health promoting apparatus 300 have been omitted.

With the health promoting apparatus 300 shown in FIG. 17, the vertical movement of the pillow part 302 generates "anteroposterior acceleration" in the head 101-1 of the user 101.

Compared to the first and second embodiments mentioned above, this third embodiment differs in that "anteroposterior acceleration" is generated in the head 101-1 of the user 101. However, the "vertical acceleration" and "anteroposterior acceleration" in the head 101-1 both generate the same level of "acceleration" in the head 101-1. As such, "movement of interstitial fluid in the brain" occurs, and the shear stress is applied to the cells exposed to the interstitial fluid. This results in the supply of "shear stress" to various local parts of the body.

With the health promoting apparatus of the present invention, various symptoms of diseases can be improved and recovery from fatigue is expected based on the physiological benefits of "moderate exercise". Thus, elderly individuals can maintain better health, which will result in a lower burden on the family in terms of long-term care. This will likely cause healthy aging in society.

LIST OF REFERENCE SIGNS

100 Health promoting apparatus
102 Seat part
103 Push rod
104 Oscillation generator
105 Oscillation controller
106 Housing

The invention claimed is:

1. A health promoting apparatus to benefit health of a user based on medical factors underlying moderate exercise, the apparatus comprising:
   an oscillation generator configured to oscillate a head of the user in a vertical direction or an anteroposterior direction; and
   an oscillation controller connected to the oscillation generator, and configured to control an oscillation generated by the oscillation generator,
   wherein the oscillation controller is configured:
      to control the oscillation generator to apply shear stress to cells in the brain of the user by moving interstitial fluid in the brain, in order to promote the health of the user;
      to set a frequency of the oscillation from 1 to 3 Hz, and
      to control acceleration applied to the head of the user from ±0.3 to 2.0×g,
   wherein the health promoting apparatus further comprises:
      a seat part to which the oscillation is applied by the oscillation generator;
      a backrest part; and
      a headrest part, and
   wherein the apparatus is configured to oscillate the head of the user in the vertical direction, in such a state that the user is seated on the seat part and the head is supported by the headrest part.

2. The health promoting apparatus according to claim 1, wherein the oscillation controller is configured to set an amplitude of the oscillation in the vertical direction to equal to or less than 8 cm.

3. The health promoting apparatus according to claim 1, wherein the oscillation controller is configured to set duration of the oscillation from 10 to 60 minutes or until the user falls asleep.

* * * * *